US00PP32395P2

(12) United States Plant Patent
Wood

(10) Patent No.: US PP32,395 P2
(45) Date of Patent: Oct. 27, 2020

(54) ***PHILADELPHUS* PLANT NAMED 'SMNPBD'**

(50) Latin Name: *Philadelphus coronarius*
Varietal Denomination: SMNPBD

(71) Applicant: Spring Meadow Nursery, Inc., Grand Haven, MI (US)

(72) Inventor: Timothy D Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 16/602,604

(22) Filed: Nov. 5, 2019

(51) Int. Cl.
*A01H 5/02* (2018.01)
*A01H 6/48* (2018.01)

(52) U.S. Cl.
USPC ..... Plt./226

(58) Field of Classification Search
USPC ..... Plt./226
CPC ..... A01H 5/02; A01H 5/00; A01H 6/48
See application file for complete search history.

(56) References Cited

PUBLICATIONS

Google search for mock orange Illuminati Arch print out on Apr. 23, 2020, 2 pp. (Year: 2020).*
Spring Meadow Flowering Shrubs Starter Plants Catalog and Shrub Reference 2019-2020, Part 1, retrieved on Apr. 23, 2020, retrieved from the Internet at https://springmeadownursery.com/files/resource_files/SMN_Wholesale_Catalog_Part_1.pdf, pp. 1-9, 21. (Year: 2020).*
Spring Meadow Flowering Shrubs Starter Plants Catalog and Shrub Reference 2019-2020, Part 2, retrieved on Apr. 23, 2020, retrieved from the Internet at https://springmeadownursery.com/files/resource_files/SMN_Wholesale_Catalog_Part_2.pdf, pp. 72-73, 98. (Year: 2020).*

* cited by examiner

*Primary Examiner* — June Hwu
(74) *Attorney, Agent, or Firm* — Cassandra Bright

(57) ABSTRACT

A new and distinct *Philadelphus* cultivar named 'SMNPBD' is disclosed, characterized by double flowers, thick foliage, and an attractive plant habit for landscape purposes. The new variety is a *Philadelphus*, normally used for outdoor ornamental purposes.

2 Drawing Sheets

Latin name of the genus and species: *Philadelphus coronarius*.
Variety denomination: 'SMNPBD'.

BACKGROUND OF THE INVENTION

The new *Philadelphus* cultivar is a product of a planned breeding program conducted by the inventor, Timothy Wood, in Grand Haven, Mich. The objective of the breeding program was to develop new forms of flowers. The open-pollination resulting in this new variety was made during Summer of 2011.

The seed parent is an unnamed, irradiated selection of *Philadelphus* 'Snowbelle'. The new variety was selected in Spring of 2015 by the inventor in a group of seedlings resulting from the 2011 open pollination, in a nursery in Grand Haven, Mich.

Asexual reproduction of the new cultivar has been performed by softwood cuttings. This was first performed at the same nursery in Grand Haven, Mich. in 2015, and has shown that the unique features of this cultivar are stable and reproduced true to type in multiple successive generations.

SUMMARY OF THE INVENTION

The cultivar 'SMNPBD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNPBD' These characteristics in combination distinguish 'SMNPBD' as a new and distinct *Philadelphus* cultivar:

1. Double flowers, with whorls of full petals throughout.
2. Thick, attractive foliage.
3. Dark green foliage.
4. Manageable plant habit suitable for landscape.

PARENT COMPARISON

Plants of the new cultivar 'SMNPBD' are similar to plants of the seed parent in most horticultural characteristics; however, plants of the new cultivar 'SMNPBD' differ in the following;

1. The new variety has thicker, more durable foliage.

COMMERCIAL COMPARISON

Plants of the new cultivar 'SMNPBD' are comparable to the commercial variety *Philadelphus* 'Snow White Fantasy', U.S. Plant Pat. No. 13,774. The two *Philadelphus* varieties are similar in most horticultural characteristics; however, the new variety 'SMNPBD' differs in the following;

1. The new variety has larger, darker green foliage than this comparator.
2. The new variety has thicker foliage than this comparator.

3. The new variety has more of a true double flower, with whorls of complete petals throughout, while this comparator has a center composed of petaloids.

BRIEF DESCRIPTION OF THE PHOTOGRAPHS

Figure 1:
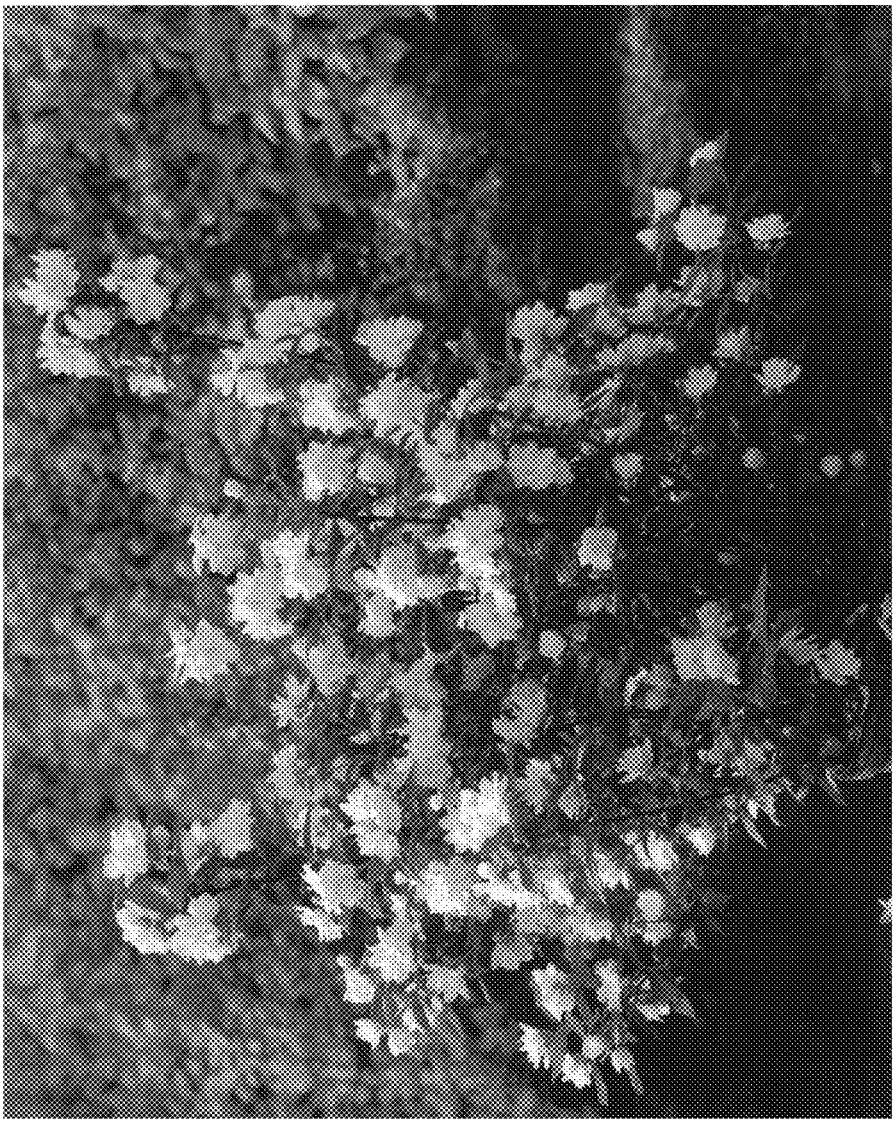

The accompanying photograph in FIG. 1 illustrates in full color a typical plant of 'SMNPBD' in the ground. Age of the plant photographed is approximately 2-3 years old from a rooted cutting.

Figure 2:
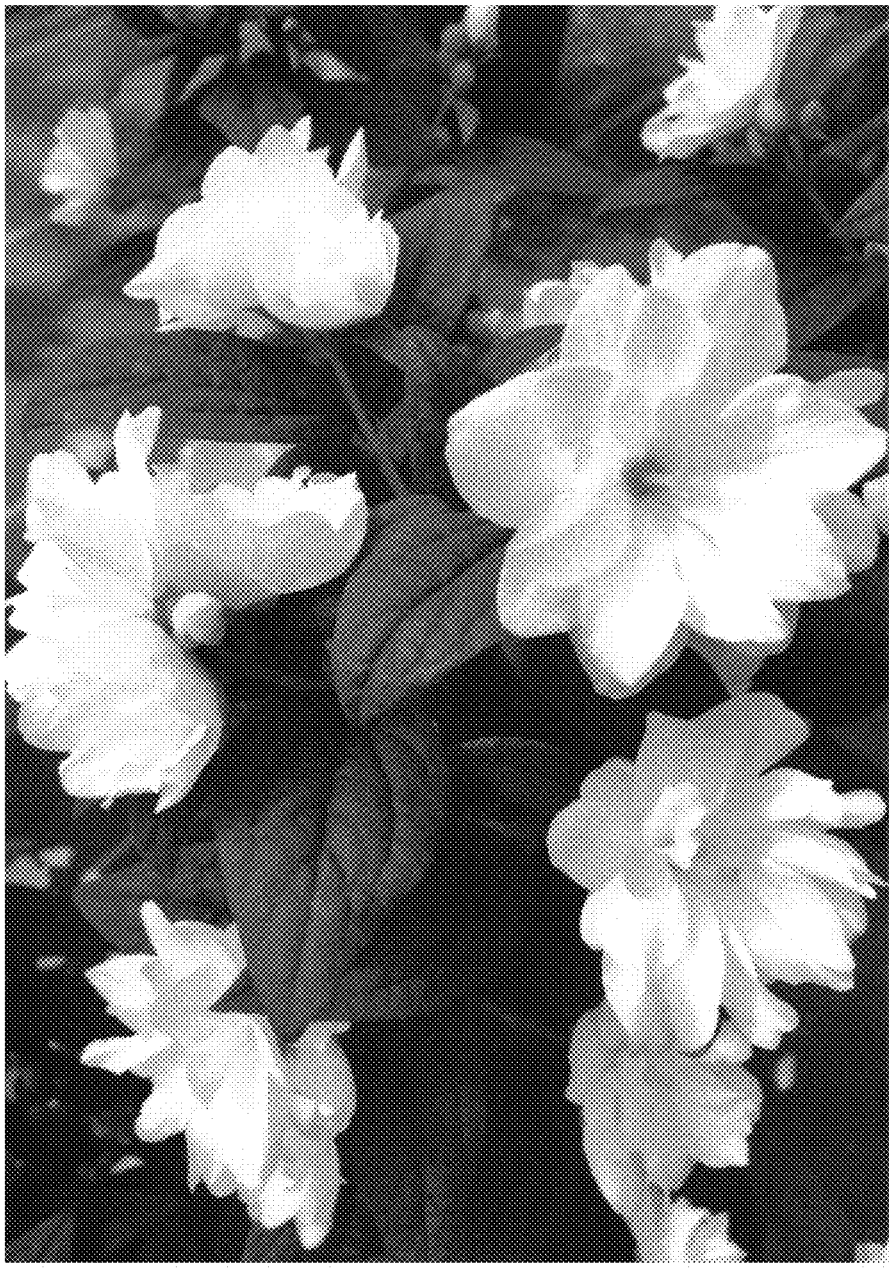

FIG. 2 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNPBD' plants grown in a poly house during Spring 2018, in Grand Haven, Mich. The growing temperature ranged from approximately 18° C. to 27° C. during the day and from approximately 5° C. to 10° C. during the night. General light conditions are normal sunlight and numerical values represent averages of typical plant types.

Botanical classification: *Philadelphus coronarius* 'SMNPBD'.

PROPAGATION

Type of propagation typically used: Softwood cuttings.
Time to initiate roots: About 2 weeks.
Time to produce a rooted cutting: About 2 months.
Root description: Thin to thick, fibrous, dense, freely branching. White to brown in color, not accurately measured with The R.H.S. Colour Chart.

PLANT

Age of plant described: 2-3 years old from a rooted cutting.
Container size: 3 gallon container.
Overall plant shape: Upright.
Growth habit: Upright.
Plant spread: 63 cm.
Plant height: 110 cm.
Growth rate: Good.
Plant vigor: Good.
Branching habit: Very upright, outwards, weeping.
Length of primary lateral branches: 61.5 cm.
Diameter of lateral branches: 0.6 cm.
Quantity of lateral branches: 10 to 15.
Stem:
- *Color*.—RHS Greyed-Brown N199B.
- *Shape*.—Round.
- *Strength*.—Strong.
- *Aspect angle*.—0-80°.
- *Pubescence*.—No.
- *Bark*.—Not observed to date.

Internode length: Average 5 cm.

FOLIAGE

Leaf:
- *Arrangement*.—Opposite, single.
- *Average length*.—6 cm.
- *Average width*.—3 cm.
- *Shape of blade*.—Ovate.
- *Apex*.—Acute to acuminate.
- *Base*.—Obtuse.
- *Margin*.—Ciliate.
- *Texture of top surface*.—Rugged.
- *Texture of bottom surface*.—Rough, distinct veins.
- *Color*.—Young foliage upper side: RHS Green 143A. Young foliage under side: RHS Green 143D. Mature foliage upper side: RHS Green 137A. Mature foliage under side: RHS Green 138B.
- *Venation*.—Type: Pinnate. Venation color upper side: RHS Yellow-Green 145B. Venation color under side: RHS Green 142D.
- *Petiole*.—Length: 8 mm. Diameter: 1.5 mm. Texture, upper side: Some pubescence. Texture, under side: Some pubescence. Color, upper side: RHS Yellow-Green 145B. Color, under side: RHS Green 142D.

FLOWER

Arrangement: Groups of axial flowers along lateral stems.
Natural flowering season: Spring.
Inflorescence form: Cyme.
Flowers and buds per inflorescence: 3-5.
Flowers and buds per plant: About 200.
Inflorescence size:
- *Width*.—5 cm.
- *Height*.—7 cm.

Individual Flowers:
- *Type*.—Rotate.
- *Quantity*.—About 30 per lateral stem.
- *Diameter*.—6 cm.
- *Length*.—6 cm.
- *Depth*.—3 cm.
- *Aspect*.—Upward, outward, or facing slightly downward.
- *Persistence*.—Self-cleaning.
- *Fragrance*.—Light and sweet.
- *Lastingness of blooms*.—3-5 days.

Petals:
- *Arrangement*.—Whorled.
- *Number*.—Average 16.
- *Shape*.—Elliptic.
- *Margin*.—Entire.
- *Tip shape*.—Obtuse.
- *Base shape*.—Truncate.
- *Length*.—2.75 cm. Innermost Petals 1.75 cm.
- *Width*.—1.75 cm. Innermost Petals 8 mm.
- *Texture*.—Upper: Smooth, delicate. Lower: Smooth, delicate.
- *Color*.—When opening: Upper surface: RHS Green-White 157D. Under surface: RHS Green-White 157D. Fully opened: Upper surface: RHS Green-White 157D. Under surface: RHS Green-White 157D.

Bud:
- *Quantity*.—20 to 25 per lateral stem.
- *Shape*.—Ovoid.
- *Length*.—2 cm.
- *Diameter*.—1 cm.
- *Color*.—RHS Green-White 157D.

Sepals:
- *Arrangement*.—Cruciform.
- *Shape*.—Tear-drop.
- *Tip shape*.—Very acute.
- *Base shape*.—Truncate.
- *Margin*.—Entire.

*Quantity per flower.*—4.
*Length.*—9 mm.
*Width.*—5 mm.
*Texture.*—Upper: Pubescent. Lower: Pubescent.
*Color.*—Upper: RHS Yellow-Green 144A. Lower: RHS Yellow-Green 144B.

Calyx tube:
*Shape.*—Cupulate.
*Length.*—5 mm.
*Diameter.*—4 mm.

Peduncle:
*Length.*—1 to 4 cm.
*Diameter.*—4 to 6 mm.
*Texture.*—Pubescent upper section, lower section glabrous.
*Angle.*—0-90°.
*Color.*—RHS Yellow-Green 144A.
*Strength.*—Good.

Pedicel:
*Length.*—4 mm.
*Diameter.*—1 mm.
*Texture.*—Pubescent.
*Angle.*—0-90°.
*Color.*—RHS Yellow-Green 144A.
*Strength.*—Good.

REPRODUCTIVE ORGANS

Stamens: Not present.

Pistil:
*Number.*—4.
*Length.*—5 mm.
*Style.*—Length: 4.5 mm. Color: RHS Green-White 157B.

Stigma:
*Shape.*—Flat.
*Color.*—RHS Green-White 157B.
*Ovary color.*—RHS Green-White 157B.

OTHER CHARACTERISTICS

Fruits and seeds: Not observed to date.

Disease/pest resistance: Neither resistance nor susceptibility to normal diseases and pests of *Philadelphus* observed.

Temperature range: Observed to tolerate a temperature range from −28° C. to 35° C. Root hardy to −28C, top of the plant does die back to the ground.

What is claimed is:

1. A new and distinct cultivar of *Philadelphus* plant named 'SMNPBD' as herein illustrated and described.

* * * * *